US00PP29214P3

(12) United States Plant Patent
White

(10) Patent No.: US PP29,214 P3
(45) Date of Patent: Apr. 10, 2018

(54) APPLE TREE NAMED 'PREMA129'

(50) Latin Name: ***Malus domestica* Mill.**
Varietal Denomination: PremA129

(71) Applicant: Allan G. White, Havelock North (NZ)

(72) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 6 days.

(21) Appl. No.: 14/998,811

(22) Filed: Feb. 18, 2016

(65) Prior Publication Data

US 2016/0255756 P1 Sep. 1, 2016

Related U.S. Application Data

(60) Provisional application No. 62/176,507, filed on Feb. 19, 2015.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Keith O Robinson
(74) *Attorney, Agent, or Firm* — Michelle Bos Legal LLC

(57) ABSTRACT

A new and distinct apple tree named 'PremA129' is disclosed. The new apple is notable for its attractive appearance, superb texture, improved flavor and long shelf life.

2 Drawing Sheets

Latin name of the genus and species of the plant claimed: *Malus domestica* Mill.

Variety denomination: 'PREMA129'.

STATEMENT REGARDING FEDERALLY SPONSORED RESEARCH OR DEVELOPMENT

None.

BRIEF DESCRIPTION OF THE VARIETY

The new variety of apple tree 'PremA129' was created in the course of a planned breeding program carried out at The New Zealand Institute for Plant and Food Research, Hawkes Bay, New Zealand. 'PremA129' originated as a result of a controlled cross of 'Scired' (seed parent, unpatented) and 'PremA280' (pollen parent, U.S. Plant Pat. No. 19,762). 'PremA129' was selected as a single plant from among a population of seedlings derived from the parents. Asexual propagation by budding was first carried out in New Zealand. The variety has since been observed over a number of asexually propagated generations, and has been found to remain true to type.

'PremA129' is distinguished from its parents 'Scired' and 'PremA280' by the following characteristics:

| | 'Scired' | 'PremA280' | 'PremA129' |
|---|---|---|---|
| Maturity | Late | Mid-season | Mid-season |
| Fruit Size | Medium | Medium | Large |
| Russet Sensitivity | Medium-High | Low | Low |

'PremA129' is distinguished from 'Tenroy Gala' (also known as 'Royal Gala', U.S. Plant Pat. No. 4,121) by the following characteristics:

| | 'Tenroy Gala' | 'PremA129' |
|---|---|---|
| Fruit Size | Medium | Large |
| Pattern of overcolor | Broad stripes | Solid flush |
| Fruit shape | Globose | Conical |

BRIEF DESCRIPTION OF THE PHOTOGRAPHS

Figure 1:
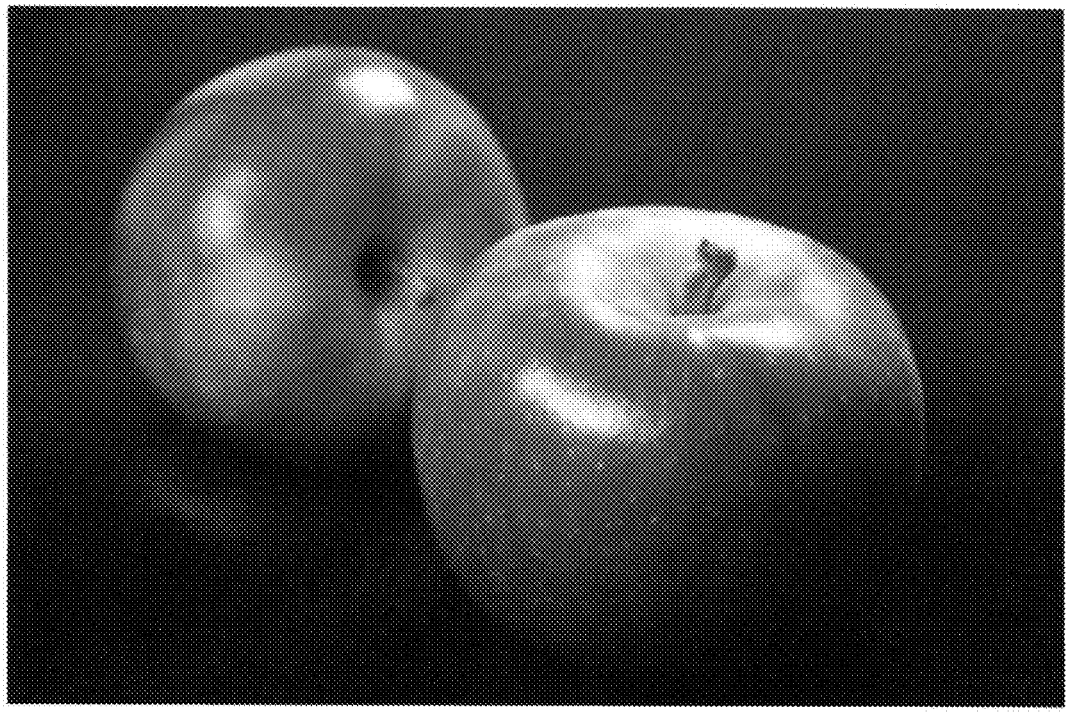
Figure 2:
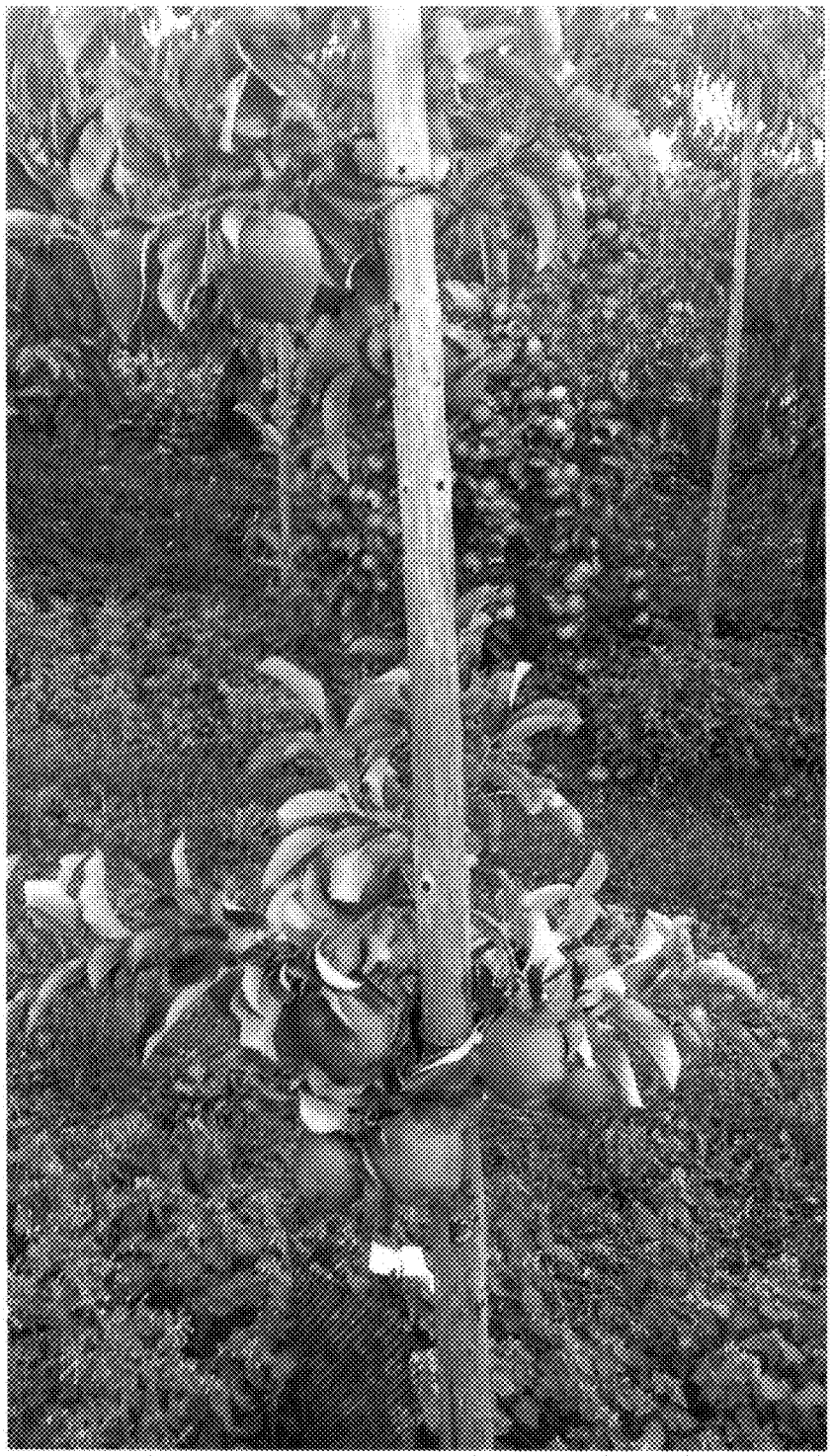

FIG. 1 shows the fruit of a 'PremA129' apple tree; and FIG. 2 shows a 'PremA129' apple tree.

DETAILED BOTANICAL DESCRIPTION OF THE VARIETY

The following detailed botanical description is based on observations of four-year-old trees made during the 2014 growing season at New Zealand. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Type*.—Ramified.
*Vigor*.—Moderate.
*Habit*.—Semi-Spreading.
*Height*.—200 cm.
*Diameter*.—85 cm.
*Trunk diameter at* 30 *cm above the graft union*).—4 cm.
*Bark texture*.—Smooth.
*Bark coloration*.—202D.
*Lenticels*.—Size 0.4 cm.
*Lenticel color*.—150D.

Branch:
*Length.*—30 cm.
*Diameter.*—1.5 cm.
*Crotch angle.*—70°.
*Color.*—Over color black 202D.
*Base color.*—Greyed-orange 174A.
*Lenticels.*—Size — 0.2 cm.
*Lenticel color.*—Yellow-green 150D.
*Quantity per inch*$^2$.—10.

1 Year old shoot:
*Length.*—30 cm.
*Color.*—Greyed-orange 174A.
*Thickness.*—0.8 cm.
*Internode length.*—4 cm.
*Lenticel size.*—0.1 cm.
*Lenticel color.*—Yellow-green 150D.
*Quantity per inch*$^2$.—12.

Flower buds:
*Quantity per spur.*—5.
*Length.*—1.1 cm.
*Width.*—0.7 cm.
*Color.*—Red-purple 64C.

Flowers:
*Color at balloon stage.*—Red-purple N66D.
*Diameter of open flower.*—5 cm.
*Relative position of petal margin.*—Not touching.
*Depth.*—0.5 cm.
*Number per cluster.*—5.

Petals:
*Number per flower.*—5.
*Length.*—2.5 cm.
*Width.*—1.5 cm.
*Margin.*—Smooth.
*Color of upper surface.*—White 155C with red-purple N66D and red-purple 68D edges.
*Color of lower surface.*—White 155C with red-purple 68D edges.

Pistils:
*Size.*—0.9 cm.
*Color.*—White 155C.

Anthers:
*Quantity.*—15.
*Size.*—0.1 cm.
*Color of pollen.*—Yellow 2B.
*Abundance of pollen.*—Moderate.

Stigma:
*Size.*—0.1 cm.
*Color.*—Yellow 2B.

Style:
*Size.*—0.8 cm.
*Color.*—White 155C.

Ovary:
*Size.*—Width — 0.4 cm, Length — 0.6 cm.
*Color.*—Green 138B.

Bloom:
*Date of first bloom.*—April 4$^{th}$.
*Date of full bloom.*—April 10$^{th}$.

Pedicel:
*Width.*—0.1 cm.
*Length.*—2.5 cm.
*Color.*—Greyed-green 194B.

Sepals:
*Quantity.*—5.
*Color.*—Greyed-green 194B.
*Length.*—1 cm.
*Width.*—0.5 cm.

Leaves:
*Length.*—8 cm.
*Width.*—4 cm.
*Blade margin.*—Serrated.
*Apex.*—Pointed.
*Base shape.*—Round.
*Color of top surface.*—Yellow-green 144A.
*Color of bottom surface.*—147C.
*Attitude in relation to shoot.*—70°.

Petiole:
*Length.*—4 cm.
*Diameter.*—0.2 cm.
*Color.*—Yellow-green 148D.

Fruit:
*Size.*—Height 71 mm, maximum diameter 69 mm.
*Shape.*—Conical.
*Ribbing.*—None.
*Depth of eye basin.*—1 cm.
*Width of eye basin.*—2 cm.
*Width of eye.*—1 cm.
*Russet around eye.*—Absent.
*Length of stalk.*—2.5 cm.
*Thickness of stalk.*—0.3 cm.
*Width of stalk cavity.*—1.5 cm.
*Depth of stalk cavity.*—0.8 cm.
*Russet around stalk cavity.*—Absent.
*Size of lenticels.*—0.1 cm.
*Background color of skin.*—Yellow-green 150C.
*Over color of skin.*—Red 46A and orange-red 34A.
*Relative area of over color.*—95%.
*Pattern of over color.*—Solid flush.
*Intensity of overcolor.*—Medium.
*Flesh firmness.*—Firm.
*Flesh texture.*—Fine.
*Juiciness.*—Moderate.
*Flesh color.*—White 155A.
*Stem color.*—Yellow-green 145B.

Seeds:
*Quantity per fruit.*—12;.
*Length.*—0.7 cm.
*Width.*—0.4 cm.
*Color.*—Greyed-orange 175B.

Harvest maturity: Mid-season.

Disease and pest resistance and susceptibility: Susceptible to black spot (*Venturia inaequalis*) and powdery mildew (*Podosphaera leucotricha*); Less susceptible to fire blight (*Erwinia amylovora*) than 'Gala.'.

Use: Fresh Market.

I claim:

1. A new and distinct apple tree substantially as shown and described herein.

* * * * *